United States Patent [19]
Challender et al.

[11] Patent Number: 5,492,147
[45] Date of Patent: Feb. 20, 1996

[54] DRY BREAK COUPLING

[75] Inventors: Gary B. Challender, Grass Lake; Russell L. Rogers, Munith; Robert A. Sterett, Jackson; Charles W. Scouten, Somerset Center, all of Mich.

[73] Assignee: Aeroquip Corporation, Maumee, Ohio

[21] Appl. No.: 373,620

[22] Filed: Jan. 17, 1995

[51] Int. Cl.$^6$ .............................. F16L 37/28; A61M 5/18
[52] U.S. Cl. ................... 137/614.05; 251/149.1; 251/149.5; 604/256; 604/905
[58] Field of Search .................. 251/149.1; 137/614.04, 137/614.05; 604/256, 905, 167

[56] References Cited

U.S. PATENT DOCUMENTS

| | | | |
|---|---|---|---|
| 4,436,519 | 3/1984 | O'Neill | 604/175 |
| 4,610,469 | 9/1986 | Wolff-Moaij | 251/149.1 |
| 4,895,346 | 1/1990 | Steigerwald | 251/149.1 |
| 4,960,412 | 10/1990 | Fink | 604/256 |
| 5,064,416 | 11/1991 | Newgard et al. | 604/256 |
| 5,092,857 | 3/1992 | Fleischhacker | 604/256 |
| 5,167,648 | 10/1992 | Jepson et al. | 604/283 |
| 5,215,538 | 6/1993 | Larkin | 251/149.1 |
| 5,269,771 | 12/1993 | Thomas et al. | 251/149.1 |
| 5,340,359 | 8/1994 | Segura Badia | 604/905 |

*Primary Examiner*—A. Michael Chambers
*Attorney, Agent, or Firm*—Emch, Schaffer, Schaub & Porcello

[57] ABSTRACT

A dry break coupling for joining together opposing passageways includes a male member and a female member, each of which includes a resiliently deformable rubber flap with cross-hair slits positioned to engage each other as the male and female members are moved axially toward their coupled position. Each of the male and female members also is provided with a normally closed but resiliently openable rubber septum position on the opposite side of its rubber flap from the engagement end of the respective members. The male member is provided with a blunt cannula which is fixed and a moveable carrier supporting the rubber septum. The female member is provided with an axially moveable support for the rubber flap and a fixed support for the rubber septum. As the male member and the female member move to the fully coupled position, the peripheral portions of the abutting rubber flaps are moved axially with the female carrier member while the central portions are prevented from moving by the fixed septum support with the result that the slits of the rubber flaps are pulled open thereby permitting the respective septums to engage each other. Further movement of the male and female members toward one another causes the moveable support for the male member septum to be retracted with the result that the cannula is urged through the resiliently openable abutting septums to open the passageway to the flow of fluid.

16 Claims, 5 Drawing Sheets

DRY BREAK COUPLING

BACKGROUND ART

The present invention is directed to a coupling for connecting opposing ends of a liquid flow line. The coupling may be characterized as an ultra low spill coupling in that when one coupling half is disconnected from the other coupling half, very little or no moisture or liquid will be spilled or remain on the face of the opposing ends. The coupling is particularly useful when handling body fluids or toxic chemicals. One prior art device directed to an injection site usable with a blunt cannula is disclosed in U.S. Pat. No. 5,167,648 which is incorporated herein by reference.

DISCLOSURE OF THE INVENTION

The present invention includes a male member and female member each of which is provided with a resiliently deformable flat rubber flap. The rubber flaps, which are provided with cross-hair slits, engage one another along a plane as the housing of the first coupling half is moved into engagement with the housing of the second coupling half. During the initial engagement, the central portions of the respective rubber flaps meet along a plane defined by the abutting outer faces of the respective rubber flaps. The rubber flaps are supported, respectively, on a female member and a male member.

The female member includes a housing having an annular wall with an open receiving end and an axially extending tubular member supported on the housing in spaced relationship with the annular wall. A slideable support sleeve encircles the tubular member and is yieldingly moveable under urging by a compression spring from a position aligned with the leading free end of the tubular member to a retracted position spaced from such free end. The rubber flap of the female member has its peripheral edge secured to the support sleeve. When the support sleeve is in its extended position, the inner surface of the rubber flap is generally aligned with the leading end of the tubular member and its central portion extending across such leading end is flat. A pre-slit rubber septum is mounted on the tubular member in axially spaced relationship with the inner surface of the rubber flap.

The male member includes a housing extending from a connection end for engagement with a source of fluids to an open free end defined by an annular wall sized to be positioned in the female member open receiving end in spaced relationship with its annular wall. An annular support member, also sized to be positioned within said female member annular wall in spaced relationship therewith, is attached to and extends from the open free end of the housing annular wall. The male member also has a rubber flap with a peripheral edge supported around the leading edge of the support member. A connector extends from the support member and has oppositely disposed cylinder defining portions sized to be received in the open receiving end of the female member in sliding engagement with the interior surface of the annular wall. The cylinder defining portions are separated by a pair of oppositely disposed planar portions. The connector clamps the peripheral edge of the male member rubber flap between it and the leading end of the annular support member.

Slidingly positioned within the housing of the male member is a carrier member which is yieldingly urgable axially from an extended position to a retracted position. A pre-slit rubber septum is mounted on the end of the carrier member and has a planar leading face which is spaced from the rubber flap of the male member. A compression spring resiliently urges the carrier member and its pre-slit rubber septum toward its extended position but permits it to be moved to a retracted position. A cannula having a blunt leading end and a central passageway is mounted on the male member housing and positioned in axial alignment with the slit of the rubber septum. The cannula extends axially to a position such that its leading end will be spaced from the leading end of the pre-slit rubber septum to permit the rubber septum to be in a closed position when the carrier member is in its extended position but will extend through and open the slit of the rubber septum upon movement of the carrier member and its rubber septum to a retracted position.

As the two halves of the coupling are joined together, the rubber flaps of the male and female members will initially contact one another along a plane defined by their respective outer surfaces. Continued movement of the male and female members toward each other causes the leading edge of the male member carrier member to push against the female member support sleeve retracting it against the urging action of its compression spring and carrying with it the peripheral portions of both rubber flaps. Such movement of the peripheral portions of the rubber flaps coupled with the stationary positioning of the leading end of the female member tubular member which prevents axial movement of the central portions of the rubber flaps, results in the central portions of such rubber flaps being pulled radially outwardly as permitted by their respective slits and stretchability of the rubber to a space between the male member carrier member and the female member tubular member and thereby permits the septum of the male member to make sealing contact with the septum of the female member at their respective leading faces. Continued axial movement of the opposing male and female members together then causes the carrier member to be retracted within the housing of the male member against the action of the compression spring with the result that the blunt leading end of the cannula carried on the male member housing extends through and forces open both the rubber septum of the male member and the rubber septum of the female member to permit the flow of liquid through the coupling and into the patient. Relative rotation between the male and female members causes them to become interlocked.

BEST MODE OF CARRYING OUT THE INVENTION

Referring to the drawings, the dry break coupling of the present invention includes two major components, namely, a male member generally designated by the numeral 10 and a female member generally designated by the numeral 20. The male member includes a housing 11 extending along an axis A from a radial shoulder 12 to a leading end 13. The housing has an exterior wall surface 14 which preferably is cylindrical throughout. Integrally formed with and extending axially from the housing 11 at the radial shoulder 12 is a connector end 15 for joining the housing 11 to a liquid supply or receiving line. The connector end 15 may have any desired configuration and, if desired, may utilize a Luer fitting of the type well-known in the medical field. A passageway 16 extends axially through the connector end 15 and the housing 11.

The housing 11 has an enlarged chamber 17 defined in part by an interior wall surface 25 parallel to axis A extending from the leading end 13 toward the radial shoulder 12 and an inwardly directed shoulder 18. Preferably, the interior wall surface 25 is cylindrical; however, it could have other cross-sectional configurations provided that it is parallel to axis A. The inwardly directed shoulder 18 has a central recess 21 in which is mounted a base member 22 having an integral blunt-nosed cannula 23 extending axially therefrom to a free end 24 which extends axially beyond the leading end 13 of housing 11.

Figure 1:
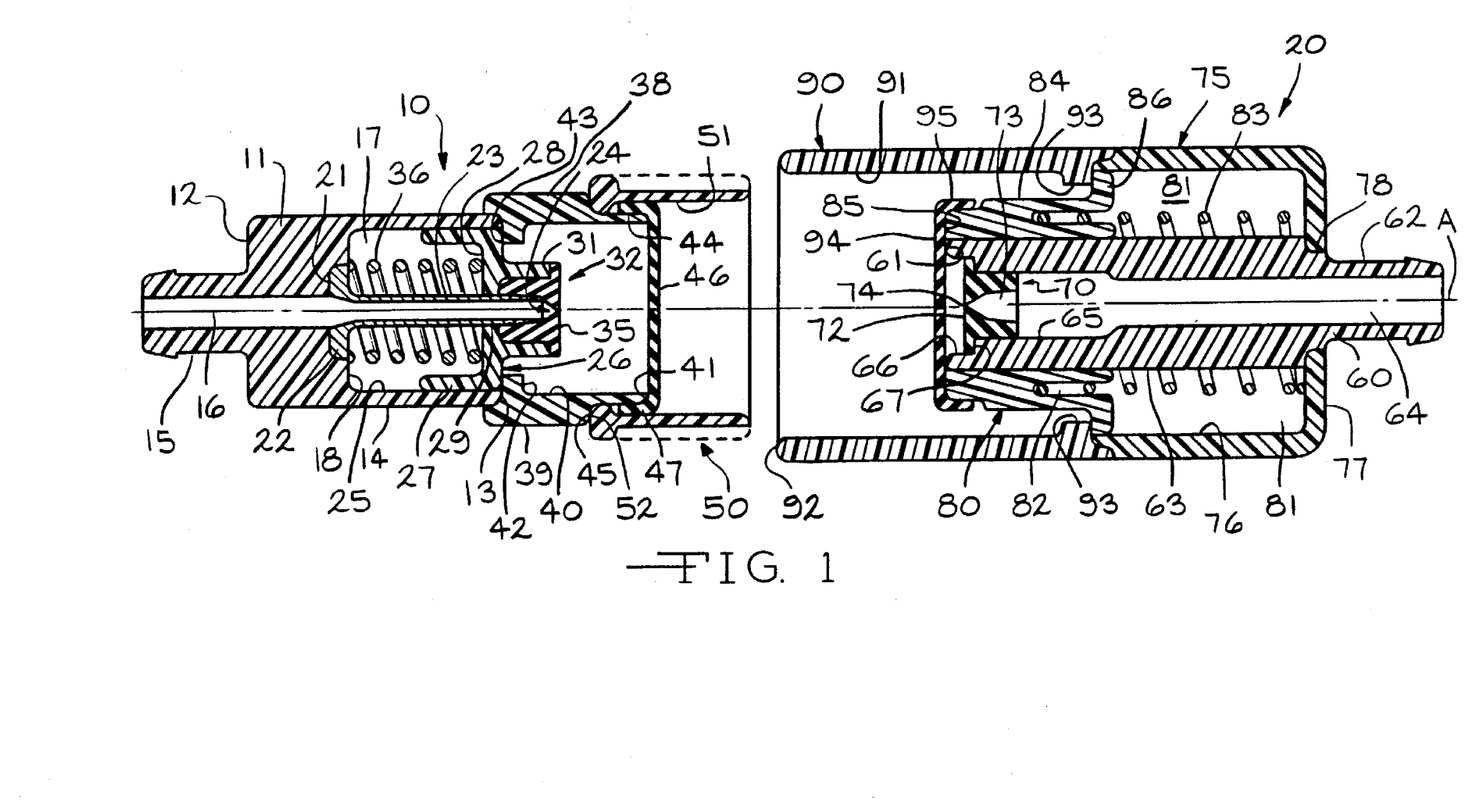
FIG. 1 is a sectional view showing the coupling of the present invention with the male member and the female member disconnected from one another.
Figure 2:
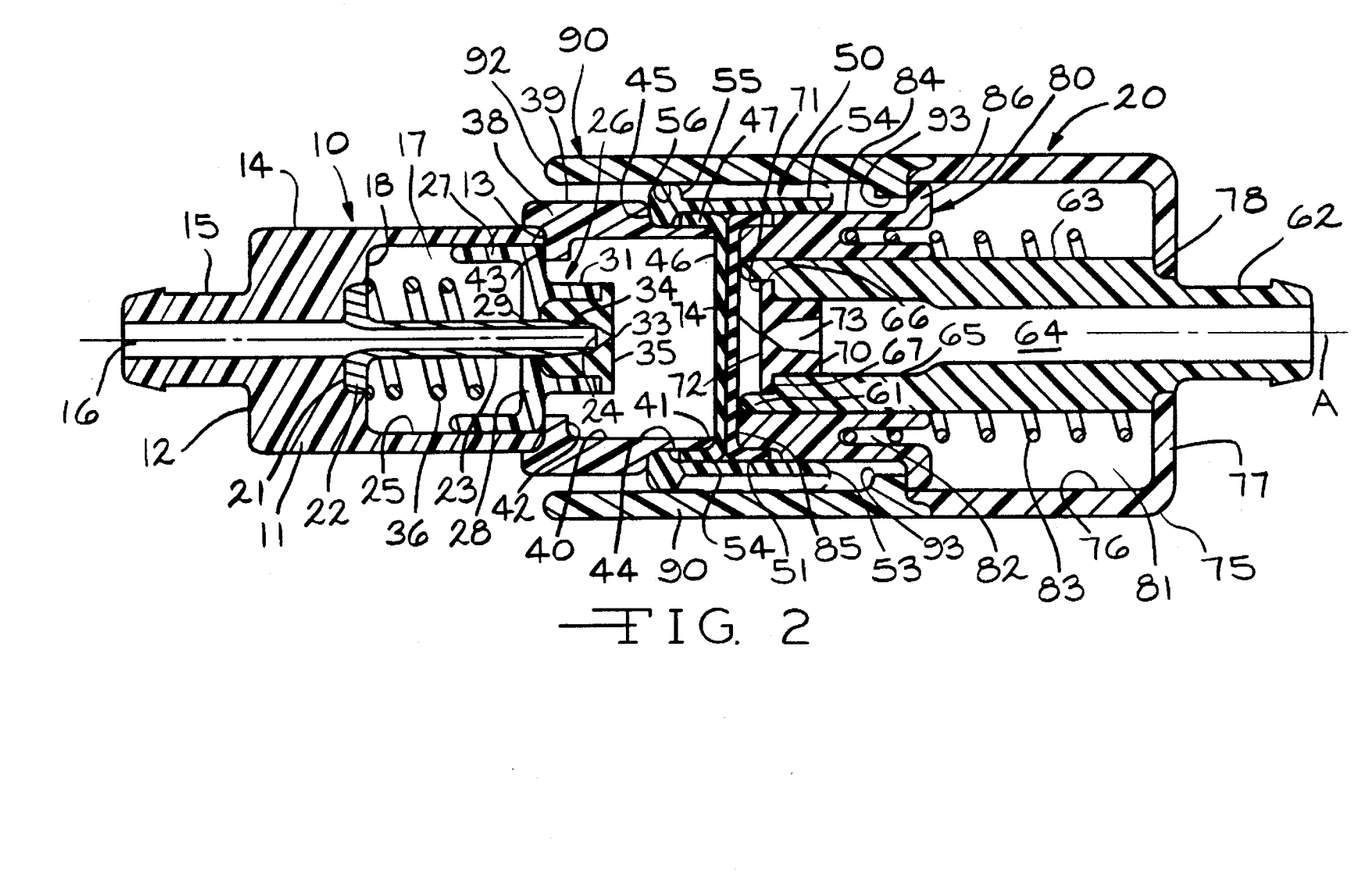
FIG. 2 is a view similar to FIG. 1 showing the position of the parts during the process of becoming engaged but before complete engagement is reached.
Figure 3:
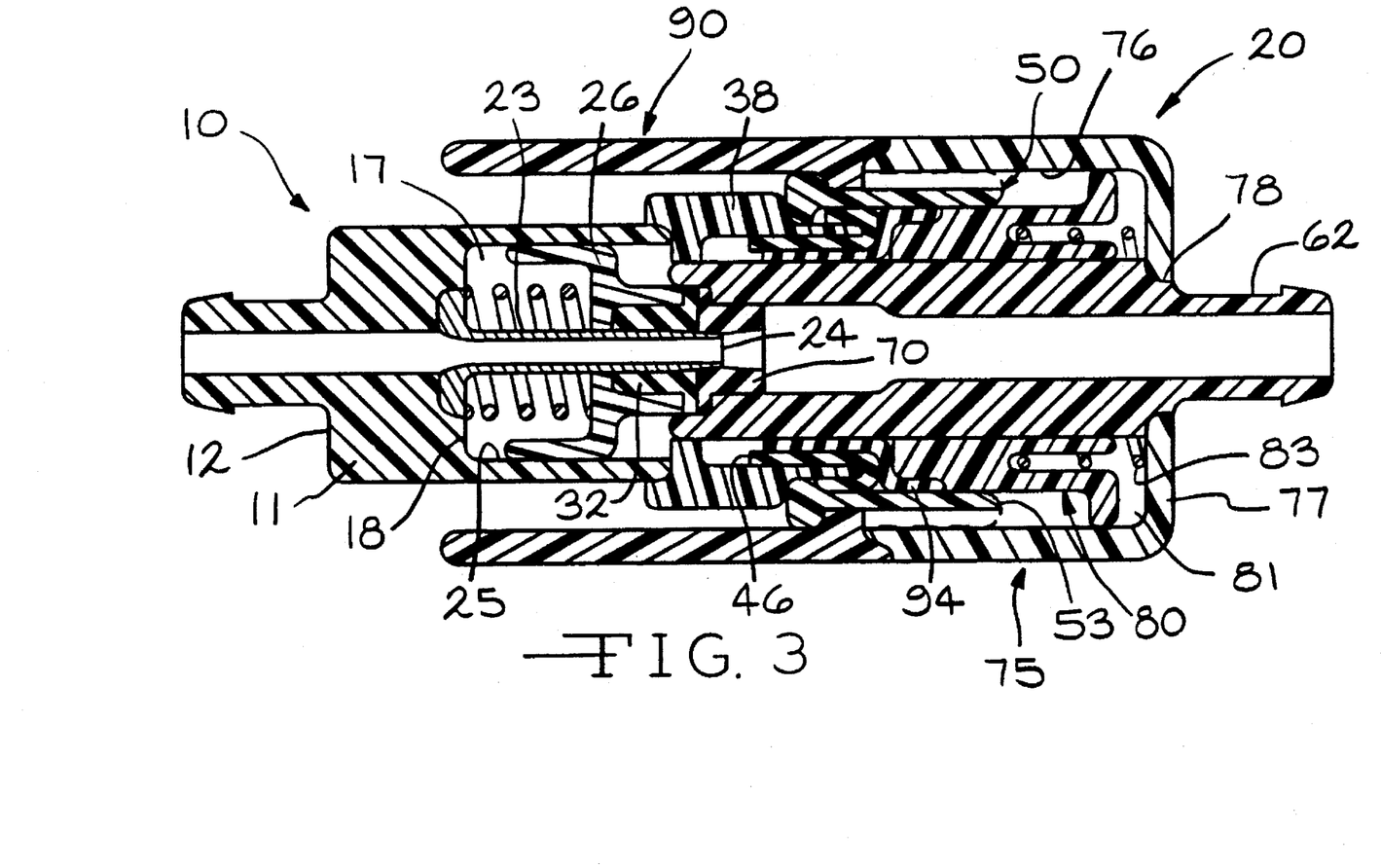
FIG. 3 is a view similar to FIGS. 1 and 2 showing the relationship of the various parts after the male member has been moved axially to a fully seated position in the female member but prior to relative rotational movement interlocking the male member to the female member.
Figure 4:
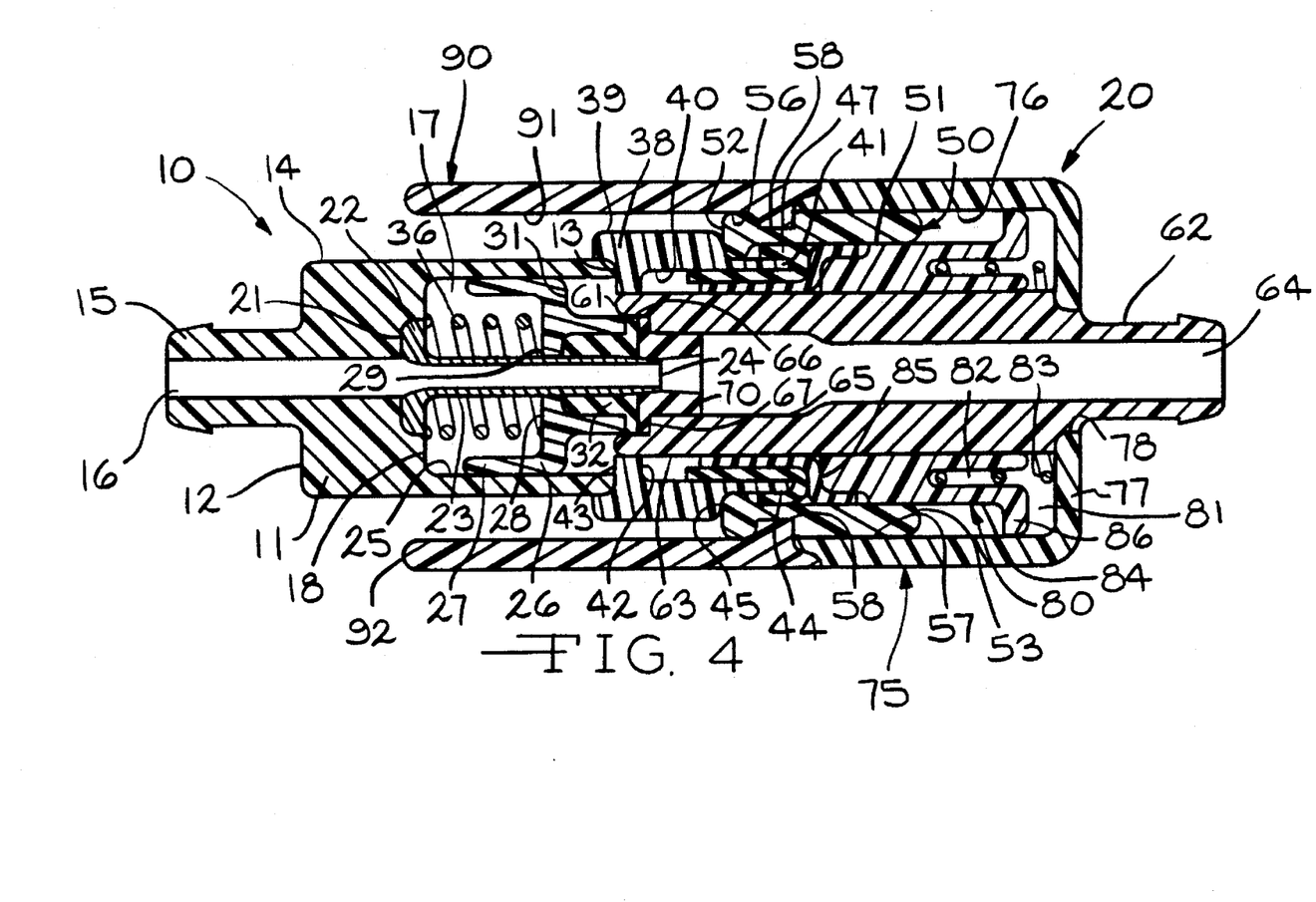
FIG. 4 is a view similar to FIG. 3 showing the relationship of the various parts when the coupling is in the fully engaged, interlocked position.

A carrier member 26 is received within the chamber 17 for axial movement from a forward position near the leading end 13 as shown in FIGS. 1 and 2 to a retracted position closer to the inwardly directed shoulder 18 (FIGS. 3 and 4). The carrier member 26 has a wall portion 27 shaped and sized to permit it to move axially within the chamber 17 in sliding engagement with the interior wall surface 25. Thus, if the interior wall surface 25 of the housing 11 is cylindrical, the wall portion 27 will have a cylindrical exterior surface. The carrier member 26 also includes a laterally extending end wall 28 having an aperture 29 through which the cannula 23 extends. An integrally formed cylindrical nose 31 of smaller diameter than the size of the wall 27 extends from the end wall 28. A rubber septum 32 is snugly fitted within the cylindrical nose 31 and can either be frictionally engaged or adhesively engaged to the carrier member 26. The rubber septum 32 extends from the carrier member end wall 28 to a flat leading face 35 and has an axial passageway 34 extending partially therethrough from the end abutting the end wall 28 toward, but not reaching, such leading face 35. A normally closed slit 33 extends from the leading face 35 to the passageway 34. The passageway 34 is sized to receive that portion of the cannula 23 adjacent the free end 24 but tapers to a size smaller than the cannula 23 and ends slightly spaced from the normally closed slit 33. Movement of the carrier member 26 and the rubber stopper 32 carried thereon from the forward position shown in FIGS. 1 and 2 to the retracted position shown in FIGS. 3 and 4 will cause the free end 24 of the cannula 23 to resiliently expand and open the slit 33 permitting the free end 24 of the cannula 23 to extend completely through the rubber stopper 32.

A compression spring 36 encircling the cannula 23 has one end abutting the inwardly directed shoulder 18 and the other end abutting the end wall 28 to resiliently urge the carrier member 26 toward the forward position shown in FIGS. 1 and 2.

Mounted on the housing 11 adjacent end 13 is a generally cylindrical housing extension 38 having an exterior wall portion 39 and an interior wall portion 40 which extends from a leading end 41 to a radially inwardly directed flange 42. The flange 42 overlies the end 13 of the housing 11 and extends radially inwardly beyond the interior surface 25 of the housing 11 to provide an abutment 43 for retaining the carrier member 26 in the chamber 17. The housing extension 38, in the area adjacent the leading end 41, has a reduced wall thickness with an exterior wall surface portion 44 having a smaller diameter than that of the cylindrical exterior wall portion 39 and cooperating therewith to define a shoulder 45.

A deformable rubber flap 46 having a cross-hair slit 48 formed therein extends laterally across the leading end 41 of the housing extension 38 and has its peripheral edge portion 47 folded therearound in contact with and engaged to the exterior wall surface portion 44, preferably with a suitable adhesive.

A connector 50 having a cylindrical interior wall portion 51 is secured to the housing extension 38 in abutting relationship with the shoulder 45 and with the cylindrical interior wall portion 51 engaging the side of the rubber flap 46 peripheral edge 47 opposite that of exterior wall surface portion 44 of the housing extension 38 thus clamping such peripheral edge 47 between it and the exterior wall surface portion 44.

The connector 50 extends axially from a trailing end 52 abutting the shoulder 45 to a leading end 53 and has an exterior which includes a pair of flat planar portions 54 disposed parallel to each other and each extending from the leading end 53 to a shoulder 55. On the opposite side of the shoulder 55 from the planar portions 54, the connector 50 has a circumferential cylindrical exterior wall portion 56. In the area axially aligned with the flat planar portions 54 are exterior wall segments 57 which are portions of a cylinder having a diameter substantially the same as that of the circumferential cylindrical wall portion 56. A major circumferential portion of each of the exterior wall segments 57 is axially spaced from the shoulder 55 and cooperate therewith to define first and second grooves 58, each of which extends in a circumferential direction from one of the planar portions 54 throughout a major circumferential extent of one of the exterior wall segments 57.

The female member 20 includes a housing 75 having a wall with a cylindrical interior surface 76 and a radially inwardly extending end 77 having an aperture 78 in which the connector end 62 of a central valve 60 is snugly positioned and supported. The central valve has a cylindrical exterior wall portion 63 with a diameter substantially smaller than the diameter of the cylindrical interior surface 76 of the housing 75. The central valve 60 extends inside the housing 75 from connector end 62 to an abutment end 61 facing in a direction to be engaged by said male member 10. The connector end 62 extends outwardly of the housing 75 and is intended to be engaged to a liquid inflow or outflow line (not shown). Although the connector end 62 and the connector end 15 of the male member 10 are each shown with enlarged bead, they may be formed to utilize any of a number of well known coupling designs for joining such connector ends 15 and 62 to fluid flow lines. Additionally, the connector end 62 may have a Luer fitting and/or a sharp cannula extending therefrom which may be inserted in a patient's arm or other body portion for extended periods of time. The central valve 60 has an exterior cylindrical wall portion 63 and a longitudinally extending passageway 64 designed to lie on the axis A when the female member 20 is engaged to the male member 10. The passageway 64 is enlarged in an area defined by an inwardly facing cylindrical wall portion 65 and is further enlarged in an area adjacent the abutment end 61 which is defined by a larger interior cylindrical wall portion 66. A shoulder 67 extends radially between the interior cylindrical wall portion 65 and the larger interior wall portion 66.

A rubber septum 70 is positioned with a major portion snugly engaging the interior cylindrical wall portion 65. The septum 70 has an outwardly extending flange 71 which abuts the shoulder 67 and at its outer radial extent, the larger interior wall portion 66. The septum 70 has a flat leading face 72 and an axial passageway 73 extending toward the leading face 72. The passageway 73 does not extend to the leading face 72. A normally closed slit 74 extends between the leading face 72 and the passageway 73 and defines a pair of lips which are normally closed but which may be urged to a separated open position by movement of the blunt-nosed cannula 23 thereinto. The leading face 72 of the septum 70 is spaced axially inwardly from the abutment end 61 and is the same size and configuration as the rubber septum 32 of the male member 10.

Encircling the exterior cylindrical wall portion 63 is a carrier member 80 which is maintained in axially slideable contact therewith and is moveable from a forward position axially aligned with the abutment end 61 (FIGS. 1 and 2) to a retracted position closer to the end 77 (FIGS. 3 and 4). The carrier member 80 cooperates with the housing 75 to define a chamber 81 through which the central valve 60 extends. The carrier member 80 has an annular groove 82 facing the chamber 81. A second compression spring 83 encircles the central valve 60 and extends from a forward end engaged in the annular groove 82 to a rearward end engaged to the housing end 77 and yieldingly urges the carrier member 80 away from the end 77. The carrier member 80 has a cylindrical exterior wall surface portion 84 which extends from a position slightly spaced from its leading end 85 to an outwardly extending flange 86 at the opposite end. The diameter of the exterior cylindrical wall surface portion 84 is nearly the same as but slightly less than the diameter of the interior cylindrical wall portion 51 of the connector 50 such that the interior cylindrical wall portion 51 may become slidingly engaged with the cylindrical exterior wall surface portion 84 as the male member and the female member are moved from the uncoupled position of FIG. 1 to the coupled position of FIG. 3.

A sleeve member 90 having an interior cylindrical wall portion 91 is secured to and extends from the housing 75. The interior cylindrical wall portion 91 has a diameter sized to permit the connector 50 of the male member 10 to be moved axially into the sleeve member 90 with the circumferential exterior wall portion 56 and the exterior wall segments 57 being in sliding engagement with the cylindrical interior wall portion 91. The cylindrical interior wall portion 91 extends from an open end 92 to a connection area defined by a pair of opposing, inwardly directed flanges 93 adjacent the end joined to the housing 75. The flanges 93 are positioned to be engaged by the flange 86 of the carrier member and serve to limit the axial movement of the carrier member 80 toward the open end 92 to a position at which its leading end 85 is substantially aligned with the abutment end 61 of the central valve 60.

Figures 5, 6, 7, 8:
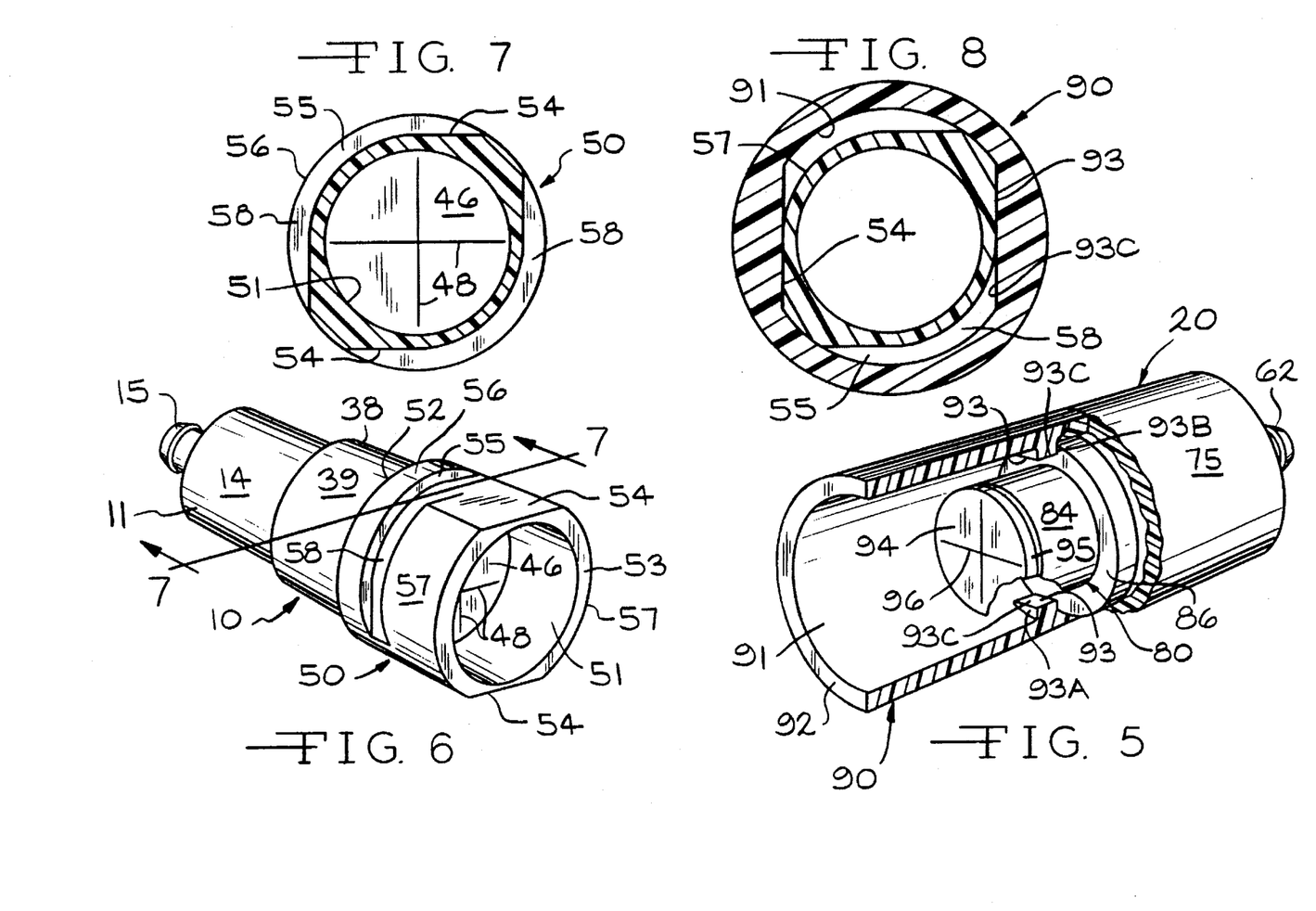
FIG. 5 is a perspective view, partially in section, of the female member.
FIG. 6 is a perspective view of the male member.
FIG. 7 is a sectional view taken through line 7—7 of FIG. 6.
FIG. 8 is a sectional view of the male member as shown in FIG. 7 engaged to the female member but with internal components omitted for clarity.

Each of the flanges 93 is defined by a leading surface 93A, (FIG. 5) a trailing surface 93B, both of which extend radially inwardly and a flat axially extending portion 93C extending between the radial portions 93A and 93B. The respective flat portions 93C of the two inwardly directed flanges 93 are parallel to one another and are spaced apart a distance slightly greater than the distance between the pair of flat planar portions 54 of the connector 50 but smaller than the diametrical distance between the opposing cylindrical exterior wall portions 57 of the connector 50. This permits the connector 50, upon proper rotational orientation relative to the sleeve member 90, to be inserted to a position at which the grooves 58 are axially aligned with the inwardly directed flanges 93. Upon such axial positioning, relative rotation between the male member 10 and the female member 20 will cause each of the inwardly directed flanges 93 to become engaged in one of the grooves 58 thereby retaining the male member 10 in a connected position to the female member 20.

A resiliently deformable rubber flap 94 substantially the same as the rubber flap 46 and having a similar cross-hair slit 96 is positioned over the leading end 85 of the carrier member 80 and has a peripheral edge 95 adhered to the reduced diameter exterior surface portion 87 of the carrier member 80.

As may be seen from the drawings, as the male member 10 is moved from the uncoupled, separated position of FIG. 1 to the fully coupled or engaged position of FIGS. 3 and 4, the connector 50 will enter the open end 92 of sleeve 90 and, upon reaching the intermediate position shown in FIG. 2 its interior cylindrical wall portion 51 will slidingly engage the cylindrical exterior wall surface portion 84 of the carrier member 80 and its opposing cylindrical exterior wall portions 57 will slidingly engage the cylindrical interior surface portion 91 of the sleeve 90. As can be seen, upon axial movement to the position shown in FIG. 2, the rubber flap 46 of the male member 10 will come into face-to-face contact with the rubber flap 94 of the female member 20. When in this position, both the rubber septum 32 of the male member 10 and the rubber septum 70 of the female member 20 will be in a closed position with the abutting lips of their respective slits 33 and 74 preventing the flow of liquid. Upon movement of the male member 10 toward engagement with the female member 20, the male member 10 should be rotatably positioned such that the planar portions 54 of its connector 50 are aligned with the flat portions 93C of flanges 93.

Continued axial movement of the male member 10 toward the end 77 of the housing 75 causes the leading end 41 of the housing extension 38 to push against the rubber flap 46 and, through it, the rubber flap 94 and carrier member 80 to move the carrier member 80 axially toward the housing end 77 against the force of the compression spring 83. Such continued movement causes the flaps 46 and 94 to open about their respective cross-hair slits 48 and 96 and to be displaced away from the axis A. Further continued movement causes such flaps 46 and 94 to be folded between the interior wall surface 40 of the housing extension 38 and the exterior cylindrical wall portion 63 of the central valve 60. Removal of such rubber flaps 46 and 94 away from the axis A then permits the cylindrical nose 31 of the carrier member 26 and the rubber septum 32 carried thereon to enter the space between the leading face 72 of the rubber septum 70 and the abutment end 61 of the central valve 60 so that the leading face 35 of the rubber septum 32 engages and seals against the leading face 72 of the rubber septum 70 with the outer surface of the nose 31 being in sliding contact with the large interior cylindrical wall portion 66 of the central valve 60. Further axial movement of the male member 10 toward the end 77 of the housing 75 will result in retraction of the carrier member 26 in the chamber 17 toward the inwardly directed shoulder 18 against the resilient urging action of the compression spring 36. Such movement of the carrier member 26 relative to the housing 11 and the cannula 23 which is mounted thereon, results in the free end 24 of the cannula extending through both the slit 33 of the rubber septum 32 and through the slit 74 of the rubber septum 70 to thereby open communication between the passageway 16 of the male member 10 and the passageway 64 of the female member 20. This is the position shown in FIG. 3.

When so positioned axially, the male member 10 may then be rotated relative to the female member 20 to thereby position the opposing flanges 93 in the respective grooves 58 to the fully engaged interlocked position shown in FIG. 4.

As will be appreciated, as the male member 10 and female member 20 become uncoupled by reverse rotation and axial movement away from each other, the rubber flap 46 and the rubber flap 94 return to the substantially flat positions shown in FIGS. 1 and 2 with the result that, even if a small amount of liquid should escape from the slit 33 of the rubber septum 32 or from the slit 74 of the rubber septum 70, it will not escape from either the male member 10 or the female member 20.

Many modifications will become readily apparent to those skilled in the art. Accordingly, the scope of the present application should be determined only by the scope of the appended claims.

We claim:

1. A coupling comprising
   (a) a male member extending along an axis including
      (1) a first septum having a normally closed, resiliently openable leading end and a rearward end;
      (2) a cannula having a forward end positioned at said first septum rearward end; and
      (3) a carrier member supporting said first septum and mounted for imparting relative movement between said first septum and said cannula from a first position in which said cannula forward end is spaced rearwardly from said first septum leading end to a second position extending through and opening said first septum leading end; and
   (b) a female member extending along an axis including
      (1) a second septum having a normally closed, resiliently openable leading end and a trailing end, said second septum leading end positioned to be engaged by said first septum leading end; and
      (2) a support member having a leading end and an opposing end, said support member, in the area of said leading end engaged to said second septum and having a passageway extending from said leading end to said opposing end;
   axial movement of said male member toward said female member along said axis causing said first septum leading end to engage said second septum leading end and continued movement causing said cannula to extend through said first septum and said second septum to open communication between said cannula and said passageway.

2. The coupling according to claim 1, further including
   (a) a housing for said male member having an annular wall encircling said first septum and said carrier, said carrier being axially moveable in said annular wall;
   (b) an annular deflector extending from said housing;
   (c) a first resilient sheet mounted on said carrier and positioned transversely of said first member axis on the opposite side of said first septum leading end from said rearward end, said resilient sheet having a central slit;
   (d) an axially moveable carrier on said female member encircling said support member and axially moveable relative thereto;
   (e) a second resilient sheet mounted on said carrier and positioned transversely of said second member axis on the opposite side of said second septum leading end from said trailing end, said axial movement of said male member toward said female member causing, prior to the engagement of said first septum leading end to said second septum leading end,
      (i) said first and second resilient sheets to become engaged with each other with annular portions thereof clamped between said annular deflector and said female member axially moveable carrier; and
      (ii) said first and second resilient sheets to have said annular portions drawn axially relative to said support member and said sheets stretched open at said slits.

3. The coupling according to claim 2, wherein said first resilient sheet is spaced from said first septum leading end and said second resilient sheet is spaced from second septum leading end.

4. The coupling according to claim 2 further including a compression spring mounted in said housing yieldingly urging said carrier member toward said first position.

5. The coupling according to claim 2 further including a second compression spring encircling said support member and yieldingly urging said axially moveable carrier said second resilient sheet.

6. The coupling according to claim 2, wherein said second septum leading end is axially spaced from said support member leading end and is axially positioned between said support member leading end and said support member opposing end.

7. A coupling according to claim 2 further including
   (a) a connector encircling said axis extending from said male member deflector, said connector having an open leading end, an internal surface sized to receive at least a portion of said female member axially moveable carrier and an exterior, said exterior including
      (i) a pair of cylinder defining portions extending from said leading end;
      (ii) a pair of substantially planar portions positioned circumferentially between said cylinder defining portions, and
      (iii) an abutment on each of said cylinder defining portions, said abutments spaced from and facing away from said leading end; and
   (b) a sleeve encircling said female member axially moveable carrier extending from an open end and having
      (i) a cylindrical interior surface sized to receive said connector, and
      (ii) a pair of flanges extending inwardly from said interior surface to an extent permitting movement of said planar portions axially thereby upon insertion of said male member but preventing movement of said cylinder defining portions axially thereby, said male member being engageable to said female member by circumferentially aligning said planar portions with said flanges, axially moving said male member relative to said female member to a position at which said connector abutments are positioned axially beyond said flanges and rotating said male member relative to said female member to engage said abutments to said flanges.

8. A coupling comprising:
(a) a female member including
  (i) a housing extending along an axis from an open receiving end to an opposing end;
  (ii) a valve mounted on said housing and extending to a leading end facing away from said housing opposing end, said valve having an axially extending passageway and a first septum positioned in said passageway, said first septum extending axially from an abutment end facing said leading end toward said opposing end, said abutment end having a normally closed, resiliently openable, slit lying on said axis, said valve having a cylindrical exterior surface portion;
  (iii) a carrier member encircling said valve in axially movable, slideable relationship with said cylindrical exterior surface portion from a forward position in the vicinity of said valve leading end to a retracted position closer to said housing opposing end;
  (iv) a compression spring urging said carrier member toward said housing receiving end;
  (v) a first flexible flap engaged to said carrier member leading end extending transversely of said axis, said first flexible flap having a slit permitting it to be moved from a substantially closed, generally planar position to an open position; and
(b) a male member movable relative to said female member along said axis from a disengaged position to an engaged position, said male member including
  (i) a housing having an end wall and an annular wall extending therefrom to a leading end, said housing having a cylindrical interior surface portion;
  (ii) a cannula mounted on said housing and having a passageway extending therethrough to an open end;
  (iii) a carrier positioned in said male member housing for axial movement in slideable engagement with said cylindrical interior surface from an extended position to a retracted position closer to said end wall;
  (iv) a second septum mounted on said carrier, said second septum having a forward end with a normally closed, resiliently openable, slit, said forward end positioned to engage said abutment end of said female member first septum, said cannula open end being spaced from said leading end and thereby permitting said slit to be closed when said carrier is in the extended position and extending through and opening said slit when said carrier is in said retracted position;
  (v) a compression spring urging said carrier toward said extended position; and
  (vi) a second flexible flap mounted on said housing leading end and extending transversely of said axis, said second flexible flap having a slit permitting it to be moved from a substantially closed generally planar position to an open position; movement of said male member into engagement with said female member causing in sequence
    (A) said second flexible flap to engage said first flexible flap with annular portions of said first and second flexible flaps being clamped between said housing leading end and said carrier member;
    (B) said carrier member to be moved axially to said retracted position carrying therewith said clamped portions of said first and second flexible flaps to open said slits thereby opening said flaps;
    (C) said second septum end to engage said first septum end; and
    (D) said male member carrier and said second septum moving to said retracted position thereby causing said cannula open end to extend through both said second septum slit and said first septum slit.

9. A coupling according to claim 8 further including
(a) a connector encircling said axis extending from said male member housing, said connector having an open leading end, an internal surface sized to receive at least a portion of said female member carrier member and an exterior, said exterior including
  (i) a pair of cylinder defining portions extending from said connector leading end;
  (ii) a pair of substantially planar portions positioned circumferentially between said cylinder defining portions, and
  (iii) an abutment on each of said cylinder defining portions, said abutments spaced from and facing away from said connector leading end; and
(b) a sleeve mounted on said female member housing and encircling said carrier member, said sleeve extending from female member housing to an open end and having
  (i) a cylindrical interior surface sized to receive said connector, and
  (ii) a pair of flanges extending inwardly from said interior surface to an extent permitting movement of said planar portions axially thereby upon insertion of said male member but preventing movement of said cylinder defining portions axially thereby, said male member being engageable to said female member by circumferentially aligning said planar portions with said flanges, axially moving said male member relative to said female member to a position at which said connector abutments are positioned axially beyond said flanges and rotating said male member relative to said female member to engage said abutments to said flanges.

10. The coupling according to claim 8, wherein said first septum abutment end is axially spaced from said valve leading end and is axially positioned between valve leading end and said housing opposing end.

11. The coupling according to claim 8, wherein said first flexible flap is spaced from said first septum abutment end and said second flexible flap is spaced from said second septum forward end.

12. A coupling comprising:
(a) a female member including
  (i) a housing extending along an axis from an open receiving end to an opposing end;
  (ii) a valve mounted on said housing and extending to a leading end facing away from said housing opposing end, said valve having an axially extending passageway and a first septum positioned in said passageway, said first septum extending axially from an abutment end facing said leading end toward said opposing end, said septum end having a normally closed, resiliently openable, slit lying on said axis, said valve having a cylindrical exterior surface portion;
  (iii) a carrier member encircling said valve in axially movable, slideable relationship with said cylindrical exterior surface portion from a forward position in the vicinity of said valve leading end to a retracted position closer to said housing opposing end;
  (iv) a compression spring urging said carrier member toward said housing receiving end; and (b) a male member movable relative to said female member along said axis from a disengaged position to an engaged position, said male member including    (i) a housing having an end wall and an annular wall extending therefrom to a leading end, said housing having a cylindrical interior surface portion;

(ii) a cannula mounted on said housing and having a passageway extending therethrough to an open end;

(iii) a carrier positioned in said male member housing for axial movement in slideable engagement with said cylindrical interior surface from an extended position to a retracted position closer to said end wall;

(iv) a second septum mounted on said carrier, said second septum having a forward end with a normally closed, resiliently openable, slit, said forward end positioned to engage said abutment end of said female member septum, said cannula open end being spaced from said leading end and thereby permitting said slit to be closed when said carrier is in the extended position and extending through and opening said slit when said carrier is in said retracted position;

(v) a compression spring urging said carrier toward said extended position;

movement of said male member into engagement with said female member causing

(A) said second septum end to engage said first septum end; and    (B) said male member carrier and said second septum moving to said retracted position thereby causing said cannula open end to extend through both said second septum slit and said first septum slit.

13. A coupling according to claim 12 further including (a) a connector encircling said axis extending from said male member housing, said connector having an open leading end, an internal surface sized to receive at least a portion of said female member carrier member and an exterior, said exterior including    (i) a pair of cylinder defining portions extending from said connector leading end;

(ii) a pair of substantially planar portions positioned circumferentially between said cylinder defining portions, and    (iii) an abutment on each of said cylinder defining portions, said abutments spaced from and facing away from said connector leading end; and (b) a sleeve mounted on said female member housing and encircling said carrier member, said sleeve extending from female member housing to an open end and having    (i) a cylindrical interior surface sized to receive said connector, and    (ii) a pair of flanges extending inwardly from said interior surface to an extent permitting movement of said planar portions axially thereby upon insertion of said male member but preventing movement of said cylinder defining portions axially thereby, said male member being engageable to said female member by circumferentially aligning said planar portions with said flanges, axially moving said male member relative to said female member to a position at which said connector abutments are positioned axially beyond said flanges and rotating said male member relative to said female member to engage said abutments to said flanges.

14. The coupling according to claim 12 wherein said first septum abutment end is axially spaced from said valve leading end and is axially positioned between valve leading end and said housing opposing end.

15. The coupling according to claim 12 further including a first flexible flap engaged to said female member carrier member leading end extending transversely of said axis, said first flexible flap having a slit permitting it to be moved from a substantially closed, generally planar position to an open position and a second flexible flap mounted on said male member housing leading end and extending transversely of said axis, said second flexible flap having a slit permitting it to be moved from a substantially closed generally planar position to an open position; movement of said male member into engagement with said female member causing said second flexible flap to engage said first flexible flap with annular portions of said first and second flexible flaps being clamped between said housing leading end and said carrier member and said female member carrier member to be moved axially to said retracted position carrying therewith said clamped portions of said first and second flexible flaps to open said slits thereby opening said flaps prior to the engagement of said second septum to said first septum.

16. A coupling according to claim 15 further including (a) a connector encircling said axis extending from said male member housing, said connector having an open leading end, an internal surface sized to receive at least a portion of said female member carrier member and an exterior, said exterior including    (i) a pair of cylinder defining portions extending from said connector leading end;

(ii) a pair of substantially planar portions positioned circumferentially between said cylinder defining portions, and    (iii) an abutment on each of said cylinder defining portions, said abutments spaced from and facing away from said connector leading end; and (b) a sleeve mounted on said female member housing and encircling said carrier member, said sleeve extending from female member housing to an open end and having    (i) a cylindrical interior surface sized to receive said connector, and    (ii) a pair of flanges extending inwardly from said interior surface to an extent permitting movement of said planar portions axially thereby upon insertion of said male member but preventing movement of said cylinder defining portions axially thereby, said male member being engageable to said female member by circumferentially aligning said planar portions with said flanges, axially moving said male member relative to said female member to a position at which said connector abutments are positioned axially beyond said flanges and rotating said male member relative to said female member to engage said abutments to said flanges.

\* \* \* \* \*